(12) United States Patent
Weser et al.

(10) Patent No.: US 9,192,556 B2
(45) Date of Patent: *Nov. 24, 2015

(54) SUBSTANCE FOR DYEING KERATIN FIBERS, INCLUDING CATIONIC ANTHRAQUINONE DYES AND FATTY ACID TRIGLYCERIDES

(71) Applicant: Henkel AG & Co. KGaA, Düsseldorf (DE)

(72) Inventors: Gabriele Weser, Neuss (DE); Claudia Kolonko, Remscheid (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/310,386

(22) Filed: Jun. 20, 2014

(65) Prior Publication Data

US 2014/0298596 A1 Oct. 9, 2014

Related U.S. Application Data

(63) Continuation of application No. PCT/EP2012/073025, filed on Nov. 20, 2012.

(30) Foreign Application Priority Data

Dec. 20, 2011 (DE) .......... 10 2011 089 220

(51) Int. Cl.
| | |
|---|---|
| *A61Q 5/10* | (2006.01) |
| *A61K 8/41* | (2006.01) |
| *A61K 8/35* | (2006.01) |
| *A61K 8/37* | (2006.01) |
| *A61Q 5/06* | (2006.01) |
| *A61K 8/92* | (2006.01) |

(52) U.S. Cl.
CPC ............... *A61K 8/416* (2013.01); *A61K 8/355* (2013.01); *A61K 8/375* (2013.01); *A61K 8/411* (2013.01); *A61K 8/922* (2013.01); *A61Q 5/065* (2013.01); *A61Q 5/10* (2013.01)

(58) Field of Classification Search
CPC ............... A61Q 5/10; A61K 8/37; C09B 1/16
USPC ................ 8/405, 552, 582, 643
See application file for complete search history.

(56) References Cited

U.S. PATENT DOCUMENTS

2010/0154139 A1* 6/2010 Giafferi et al. .......... 8/408

FOREIGN PATENT DOCUMENTS

| CA | 2613049 | * | 11/2007 | ........... A61Q 5/10 |
|---|---|---|---|---|
| CA | 2613049 A1 | | 4/2008 | |
| DE | 102009054569 A1 | * | 10/2010 | ........... A61K 8/97 |
| EP | 1006154 B1 | | 6/2000 | |
| EP | 1820826 A1 | * | 9/2006 | ........... A61Q 5/10 |
| EP | 1820826 A1 | | 8/2007 | |
| EP | 2198843 A1 | | 6/2010 | |
| EP | 2329809 A1 | | 6/2011 | |
| WO | 2006136303 A1 | | 12/2006 | |
| WO | 2008022958 A2 | | 2/2008 | |

OTHER PUBLICATIONS

STIC Search Report dated Aug. 25, 2014.*
English translation (Sep. 9, 2014) of the Pastent DE 102009054569 A1.*

* cited by examiner

*Primary Examiner* — Eisa Elhilo
(74) *Attorney, Agent, or Firm* — Steven L. Nichols; Fabian VanCott

(57) ABSTRACT

The present disclosure provides an agent for coloring keratinic fibers comprising, in a cosmetic carrier (a) at least one compound of formula (I) and (b) at least one fatty acid triglyceride. The present disclosure also provides a method of using such an agent to produce increased shine, an intense color result with improved fastness properties, or reduced selectivity.

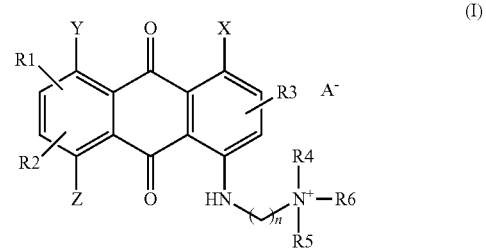

20 Claims, No Drawings

SUBSTANCE FOR DYEING KERATIN FIBERS, INCLUDING CATIONIC ANTHRAQUINONE DYES AND FATTY ACID TRIGLYCERIDES

RELATED DOCUMENTS

The present application claims the benefit and is a U.S. continuation patent application under 35 U.S.C. 111(a) and claims the right of priority under 35 U.S.C. 365 to international patent Application No. PCT/EP2012/073025, filed Nov. 20, 2012, entitled "SUBSTANCE FOR DYEING KERATIN FIBERS, INCLUDING CATIONIC ANTHRAQUINONE DYES AND FATTY ACID TRIGLYCERIDES" which claims benefit of German application No.: 102011089220.6, filed Dec. 20, 2011, these applications are herein incorporated by reference in their entirety

FIELD OF THE INVENTION

The present specification relates generally to agents for coloring and optionally simultaneously lightening keratinic fibers. More specifically, the present application relates to cosmetic agents including cationic anthraquinone dyes and special fatty acid triglycerides. The present specification also relates to the use of these agents to produce hair colors having increased shine, an intense color result, improved fastness properties and reduced selectivity.

BACKGROUND OF THE INVENTION

As a general rule, either substantive dyes or oxidation dyes are used for coloring keratinic fibers. Although intense colors with good fastness properties may be obtained with oxidation dyes, the development of the color generally takes place under the influence of oxidizing agents such as $H_2O_2$ for example, which in some cases may result in damage to the fiber. Furthermore, some oxidation dye precursors or certain mixtures of oxidation dye precursors may have a sensitizing effect on people with sensitive skin.

For temporary colors, coloring or tinting agents are conventionally used which include substantive dyes as the coloring component. These are dye molecules which attach directly to the hair and require no oxidative process to develop the color. Substantive dyes are applied under gentler conditions. The disadvantage of these dyes, however, lies in the fact that the colors often have inadequate fastness properties, in particular with regard to hair washing, but also with respect to external influences, such as sunlight, or reactive environmental chemicals, such as swimming pool water, for example. Such colors are also generally significantly more sensitive to shampooing than oxidative colors, such that an often undesired shift in shade or even a visible decolorization then occurs very much more quickly.

Achieving a uniform coloring of hair that has been frequently treated, such as for example bleached or permanently waved hair, where the fiber presents differing degrees of pre-existing damage in the various lengths or variously treated areas, represents a particular challenge in terms of coloring hair with substantive dyes. During the coloring process itself, the coloring agent may exhibit an uneven coloring behavior on hair with differing degrees of pre-existing damage, while repeated hair washing may also cause the dyes to be washed out of the different areas of the hair to varying degrees, resulting in an inconsistent, and hence undesirable color result.

In the development of coloring products based on substantive dyes, there is therefore still a particular focus on producing dye formulations having reduced selectivity, meaning that a uniform color result may be achieved on sections of the hair that have varying degrees of pre-existing damage. In particular, this reduced selectivity should still be present not only immediately after the coloring process, but also after repeated hair washes.

An object of the present specification is therefore to provide a coloring agent for keratinic fibers, in particular human hair, which, in addition to other positive fastness properties, has in particular a low selectivity (or a good equalizing capacity) and good wash fastness.

The colors achieved with the agents according to the present specification should deliver a brilliant and intense color result, both immediately after the coloring process and after repeated hair washes. Following application of the coloring agent, the hair should be uniformly colored, even in cases where the hair exhibits varying degrees of pre-existing damage, wherein this uniformity in the color result should still be present even after repeated hair washes.

In the present specification, another object is to provide brilliant and neutral shades in the blue range with the aforementioned advantageous fastness properties, said shades being extremely suitable for matting. In addition, the application of the agents should increase the shine of the hair and prevent the scalp from drying out.

The use of cationic anthraquinone dyes in products for coloring keratinic fibers is already known in principle from the prior art, for example from EP 1 006 154 B1 or EP 1 820 826 A1. Furthermore, combinations of cationic anthraquinone dyes with oxidation dye precursors of the developer type are claimed in EP 2 329 809 for the oxidative coloring of hair.

Combinations of cationic anthraquinones with special fatty acid triglycerides have not yet been described.

During the course of the work leading to the agents of the present disclosure, it was surprisingly found that combinations of cationic anthraquinone dyes and special fatty acid triglycerides lead to colors which achieve the above object to an outstanding degree.

Furthermore, other desirable features and characteristics of the present invention will become apparent from the subsequent detailed description of the invention and the appended claims, taken in conjunction with this background of the invention.

BRIEF SUMMARY OF THE INVENTION

The present specification firstly provides an agent for coloring (which may also simultaneously lighten) keratinic fibers comprising, in a cosmetic carrier,
(a) at least one compound of formula (I):

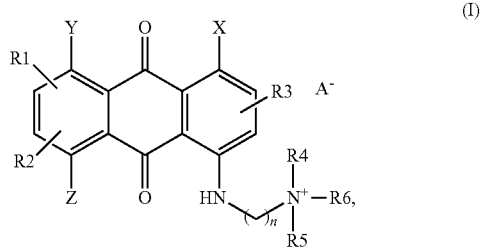

in which:

R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:

R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;

n denotes an integer between 2 and 6 inclusive; and

A⁻ denotes a physiologically acceptable anion, and (b) at least one fatty acid triglyceride.

The present specification secondly provides a method of using a cosmetic agent for coloring keratinic fibers in order to produce increased shine, an intense color result with improved fastness properties, or reduced selectivity. The method comprises:

(A) applying an agent for coloring, and optionally simultaneously lightening, keratinic fibers comprising, in a cosmetic carrier, (i) at least one compound of formula (I):

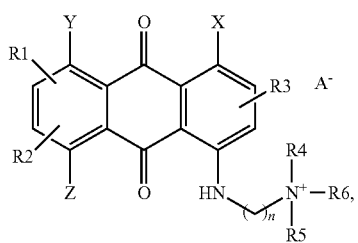

in which:

R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:

R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group, wherein at least one of the residues X, Y and Z denotes an N(R7)(R8) group;

n denotes an integer between 2 and 6 (inclusive);

A⁻ denotes a physiologically acceptable anion;

and (ii) at least one fatty acid triglyceride; and (B) after a contact time, rinsing the agent from the keratinic fibers.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In the context of the present specification, "keratin-containing fibers," "keratinic fibers," or similar terminology is understood to mean all animal hair, for example wool, horsehair, angora hair, fur, feathers and products or textiles manufactured therefrom. The keratinic fibers are, however, preferably human hair.

The term "coloring of keratin fibers" in the context of the present specification includes any form of color changing of fibers. It includes in particular the color changes covered by the terms tinting, lightening, bleaching, peroxiding, oxidative coloring, semipermanent coloring, permanent coloring and temporary coloring. It also includes color changes according to the present specification presenting a lighter color result in comparison to the original color, such as, for example, combined coloring and bleaching processes.

The agents according to the present specification include the cationic anthraquinone(s) of formula (I) and the fatty acid triglyceride(s) in a cosmetic carrier, preferably in a suitable aqueous, alcoholic or aqueous-alcoholic carrier. For the purposes of hair coloring, such carriers are for example creams, emulsions, gels or surfactant-containing foaming solutions, such as for example shampoos, foam aerosols, foam formulations or other preparations which are suitable for use on the hair. It is also possible, however, for the agents according to the present specification to be integrated into a formulation in powder or tablet form.

In the context of the present specification, aqueous-alcoholic solutions are understood to be aqueous solutions including 3 to 70 weight percent (wt. %) of a $C_1$ to $C_4$ alcohol, in particular ethanol or isopropanol. The agents according to the present specification may additionally include further organic solvents, such as for example methoxybutanol, benzyl alcohol, ethyl diglycol or 1,2-propylene glycol. All water-soluble organic solvents are preferred here.

The first essential ingredient (a) of the agents according to the present specification is at least one substantive cationic anthraquinone dye of the general formula (I).

The substituents R1 to R8 of the compound of formula (I) are described below by way of non-limiting examples: Examples of a $C_1$-$C_6$ alkyl group are the methyl, ethyl, propyl, isopropyl, n-butyl, s-butyl and t-butyl, n-pentyl and n-hexyl groups. Propyl, ethyl and methyl are preferred alkyl residues. Examples of a $C_2$-$C_6$ alkenyl group are vinyl, allyl, but-2-enyl, but-3-enyl and isobutenyl, preferred $C_2$-$C_6$ alkenyl residues being vinyl and allyl. Preferred examples of a $C_1$-$C_6$ hydroxyalkyl group are a hydroxymethyl, 2-hydroxyethyl, 2-hydroxypropyl, 3-hydroxypropyl, 4-hydroxybutyl, 5-hydroxypentyl and 6-hydroxyhexyl group; a 2-hydroxyethyl group is particularly preferred. $C_1$-$C_6$ alkoxy groups that are preferred according to the present specification are the methoxy or ethoxy group. Examples of halogen atoms are F, Cl, Br or I atoms, with Br or $C_1$ atoms being most particularly preferred. Preferred examples of $C_1$-$C_6$ alkoxy $C_2$-$C_6$ alkyl groups according to the present specification are the methoxyethyl, ethoxyethyl, methoxypropyl, methoxybutyl, ethoxypropyl, ethoxybutyl and methoxyhexyl group. Examples of a $C_1$-$C_6$ acyl amino group are the acetamide group, the propanamide group and the butanamide group, the acetamide group being preferred. The pyrrolidinium ring, the piperidinium ring, the morpholinium ring and the 1-azepanium ring may be mentioned as preferred examples of a 5-, 6- or 7-membered ring formed from R4, R5 and the quaternary nitrogen atom.

Dyes of formula (I) in which R1, R2 and R3, independently of one another, denote hydrogen, halogen, a carboxyl group, a sulfonic acid group, a $C_1$-$C_6$ alkyl group or a $C_1$-$C_6$ alkoxy group deliver particularly intense color results and are therefore preferred.

It is furthermore preferable for one of the residues selected from R1, R2 and R3 to denote halogen, a carboxyl group, a sulfonic acid group, a $C_1$-$C_6$ alkyl group or a $C_1$-$C_6$ alkoxy group and for the other two residues selected from R1, R2 and R3 both to denote hydrogen.

A preferred example is an agent for coloring, and optionally simultaneously lightening, keratinic fibers, which is characterized in that it includes a compound of formula (I) in which at least one of the residues R1, R2 and/or R3 denotes a $C_1$-$C_6$ alkyl group.

In the case of particularly suitable compounds of formula (I), one of the residues selected from R1, R2 and R3 denotes a $C_1$-$C_6$ alkyl group and the other two residues selected from R1, R2 and R3 denote hydrogen.

In a most particularly preferred example, R1 and R2 both denote a hydrogen atom and R3 denotes a methyl group.

Furthermore, particularly good coloring results are obtained with agents including at least one compound of formula (I) in which the residues R4, R5 and R6, independently of one another, denote a $C_1$-$C_6$ alkyl group or an alkenyl group. In particular, each of the residues R4, R5 and R6 preferably denotes a $C_1$-$C_6$ alkyl group.

It is most particularly preferable for R4 and R5 both to denote a methyl group and for R6 to denote a methyl group, an ethyl group or an n-propyl group.

It is moreover most particularly preferable for R4 and R5 both to denote a methyl group and for R6 to denote an n-propyl group.

In a likewise particularly preferred example, each of the residues R4, R5 and R6 denotes a methyl group.

For compounds of formula (I) there is the proviso that at least one of the residues X, Y and Z denotes an N(R7)(R8) group. Colors having good application properties were obtained in particular when compounds of formula (I) were used in which X denotes an N(R7)(R8) group and Y and Z each denote hydrogen.

R7 and R8, preferably (and independently of one another) denote hydrogen or a $C_1$-$C_6$ alkyl group. R7 and R8, particularly preferably (also independently of one another) denote hydrogen or a methyl group. Compounds of formula (I) in which both R7 and R8 denote hydrogen have proved to be particularly suitable and are therefore particularly preferred.

In the context of the work leading to the agents of the present disclosure it has proved most particularly advantageous for X to denote an $NH_2$ group.

A further preferred example is therefore an agent for coloring, and optionally simultaneously lightening, keratinic fibers, which is characterized in that it includes a compound of formula (I) in which at least X denotes an $NH_2$ group.

n preferably denotes the numbers 2 or 3 and most particularly preferably the number 3.

$A^-$ denotes a physiologically acceptable anion. Suitable physiologically acceptable anions are halide, hydrogen sulfate, ½ sulfate, benzene sulfonate, p-toluenesulfonate, acetate, citrate, lactate, ½ tartrate, methosulfate ($H_3COSO_3^-$) or trifluoromethane sulfonate. $A^-$ particularly preferably denotes bromide or methosulfate ($H_3COSO_3^-$), with $A^-$ most particularly preferably denoting methosulfate ($H_3COSO_3^-$).

Agents for coloring, and optionally simultaneously lightening, keratinic fibers that are preferred according to the present specification are characterized in that they include at least one compound of the general formula (I) selected from 3-[(4-amino-9,10-dihydro-3-methyl-9,10-dioxo-1-anthracenyl)amino]-N,N,N-trimethyl-1-propanaminium methosulfate 3-[(4-amino-9,10-dihydro-3-methyl-9,10-dioxo-1-anthracenyl)amino]-N,N,N-trimethyl-1-propanaminium bromide, 3-[(4-amino-9,10-dihydro-3-methyl-9,10-dioxo-1-anthracenyl)amino]-N,N,N-trimethyl-1-propanaminium chloride, 3-[(4-amino-9,10-dihydro-3-methyl-9,10-dioxo-1-anthracenyl)amino]-N,N,N-trimethyl-1-propanaminium-p-toluenesulfonate, 3-[(4-amino-9,10-dihydro-3-methyl-9,10-dioxo-1-anthracenyl)amino]-N,N,N-trimethyl-1-propanaminium acetate, 3-{[9,10-dihydro-4-(methylamino)-9,10-dioxo-1-anthracenyl]amino}-N,N-dimethyl-N-propyl-1-propanaminium methosulfate, 3-{[9,10-dihydro-4-(methylamino)-9,10-dioxo-1-anthracenyl]amino}-N,N-dimethyl-N-propyl-1-propanaminium bromide, 3-{[9,10-dihydro-4-(methylamino)-9,10-dioxo-1-anthracenyl]amino}-N,N-dimethyl-N-propyl-1-propanaminium chloride, 3-{[9,10-dihydro-4-(methylamino)-9,10-dioxo-1-anthracenyl]amino}-N,N-dimethyl-N-propyl-1-propanaminium-p-toluenesulfonate and 3-{[9,10-dihydro-4-(methylamino)-9,10-dioxo-1-anthracenyl]amino}-N,N-dimethyl-N-propyl-1-propanaminium acetate.

The compound of formula (Ia) has proved to be an ideally suitable compound of formula (I) for achieving the object according to the present specification

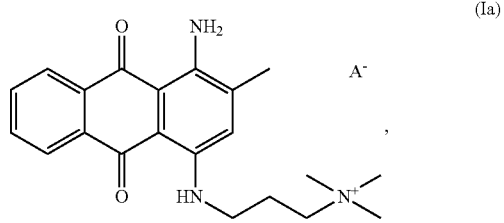

(Ia)

in which $A^-$ denotes a physiologically acceptable anion, preferably methosulfate ($H_3COSO_3^-$).

A further particularly preferred example is therefore an agent for coloring, and optionally simultaneously lightening, keratinic fibers, which is characterized in that it includes as the compound of formula (I) the compound according to formula (Ia),

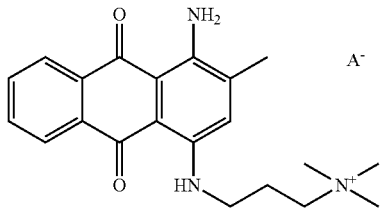
(Ia)

in which A⁻ denotes a physiologically acceptable anion, preferably methosulfate ($H_3COSO_3^-$).

The agents according to the present specification for coloring, and optionally simultaneously lightening, keratin fibers include the compound(s) of formula (I) preferably in amounts above 0.0001 wt. % and below 5 wt. %, relative in each case to the total agent.

A preferred example is an agent which includes the compound(s) of formula (I) in an amount of from 0.0001 to 5 wt. %, preferably from 0.005 to 3.5 wt. %, particularly preferably from 0.01 to 2.5 wt. %, in particular from 0.05 to 1.5 wt. %, and in particular preferably from 0.01 to 1.0 wt. %, relative in each case to the total weight of the agent.

As the second essential constituent of the formulation (b), the agents according to the present specification include at least one fatty acid triglyceride.

In the context of the present specification, a fatty acid triglyceride is understood to be the triester of the trihydric alcohol glycerol with three equivalents of fatty acid. The trihydric alcohol glycerol may be esterified with structurally identical, different fatty acids, or combinations thereof (for example, two identical fatty acids and a third fatty acid that is not identical to the other two).

According to the present specification, fatty acids are understood to be saturated or unsaturated, unbranched or branched, unsubstituted or substituted $C_8$-$C_{24}$ carboxylic acids. Unsaturated fatty acids may be mono- or polyunsaturated. In the case of an unsaturated fatty acid the C═C double bond(s) thereof may have either the cis- or trans-configuration.

Particularly suitable representatives of fatty acid triglycerides (b) are encompassed by formula (II):

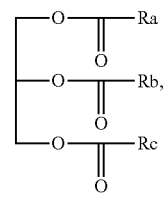
(II)

in which:
Ra, Rb, Rc independently of one another, denote a saturated or unsaturated, unbranched or branched, unsubstituted or substituted $C_7$-$C_{23}$ alkyl group.

Examples of particularly suitable fatty acid triglycerides are characterized in that at least one of the ester groups is formed from glycerol with a saturated fatty acid. In this context a fatty acid selected from the following is preferably used as the saturated fatty acid:

TABLE 1

Exemplary F groups which may provide Ra, Rb and/or Rc.

| Fatty acid | | Ra, Rb and/or Rc = |
|---|---|---|
| F1 | Octanoic acid (caprylic acid) | —$C_7H_{15}$ |
| F2 | Decanoic acid (capric acid) | —$C_9H_{19}$ |
| F3 | Dodecanoic acid (lauric acid) | —$C_{11}H_{23}$ |
| F4 | Tetradecanoic acid (myristic acid) | —$C_{13}H_{27}$ |
| F5 | Hexadecanoic acid (palmitic acid) | —$C_{15}H_{31}$ |
| F6 | Octadecanoic acid (stearic acid) | —$C_{17}H_{35}$ |
| F7 | Eicosanoic acid (arachidic acid) | —$C_{19}H_{39}$ |
| F8 | Docosanoic acid (behenic acid) | —$C_{21}H_{43}$ |
| F9 | Tetracosanoic acid (lignoceric acid) | —$C_{23}H_{47}$ |

Within this example, it is particularly advantageous for the agent to include a fatty acid triglyceride (b) in which at least one saturated $C_{14}$-$C_{20}$ fatty acid forms an ester with glycerol.

Particularly preferred compounds of the general formula (II) are thus compounds in which at least one of the residues selected from Ra, Rb and/or Rc denotes a saturated, unbranched or branched, unsubstituted or substituted $C_{13}$-$C_{19}$ alkyl group.

Compounds of formula (II) in which at least one of the residues selected from Ra, Rb and/or Rc denotes the residue —$C_{13}H_{27}$ (F4), —$C_{15}H_{31}$ (F5), —$C_{17}H_{35}$ (F6) and/or —$C_{19}H_{39}$ (F7) are most particularly suitable.

The fatty acid triglycerides in which at least one of the ester groups is formed starting from glycerol with a mono- or polyunsaturated fatty acid are also extremely suitable. A fatty acid selected from the following is preferably used as the unsaturated fatty acid:

TABLE 2

Further exemplary F groups which may provide Ra, Rb and/or Rc.

| | Fatty acid | Ra, Rb and/or Rc = |
|---|---|---|
| F11 | Petroselic acid [(Z)-6-octadecenoic acid] | |
| F12 | Palmitoleic acid [(9Z)-hexadec-9-enoic acid] | |
| F13 | Oleic acid [(9Z)-octadec-9-enoic acid] | |
| F14 | Elaidic acid [(9E)-octadec-9-enoic acid] | |
| F15 | Erucic acid [(13Z)-docos-13-enoic acid] | |

TABLE 2-continued

Further exemplary F groups which may provide Ra, Rb and/or Rc.

| Fatty acid | Ra, Rb and/or Rc = |
|---|---|
| F16 Linoleic acid [(9Z, 12Z)-octadeca-9,12-dienoic acid | |
| F17 Linolenic acid [(9Z,12Z,15Z)-octadeca-9,12,15-trienoic acid | |
| F18 Elaeostearic acid [(9Z,11E,13E)-octadeca-9,11,13-trienoic acid] | |
| F19 Arachidonic acid [(5Z,8Z,11Z,14Z)-eicosa-5,8,11,14-tetraenoic acid] | |
| F20 Nervonic acid [(15Z)-tetracos-15-enoic acid] | |

During the course of the work leading to the agents of the present disclosure, it also proved to be preferable for the coloring agent to include at least one fatty acid triglyceride (b) in which at least one ester bond of glycerol is formed with a mono-, di- or tri-unsaturated $C_{16}$-$C_{20}$ fatty acid. It is preferable in particular for at least one of the fatty acids selected from palmitoleic acid (F12), oleic acid (F13), linoleic acid (F16) and/or linolenic acid (F17) to be esterified with glycerol.

The fatty acid triglycerides of formula (II) in which at least one of the residues Ra, Rb and/or Rc denotes one of the residues F12, F13, F16 and/or F17 have thus also proved to be particularly advantageous.

The fatty acids used to form the esters in the fatty acid triglycerides (b) may also bear one or more substituents. Substituted fatty acids preferably bear one or more substituents selected from a hydroxyl group, a carbonyl group and a $C_1$-$C_6$ alkoxy group. The fatty acids are preferably substituted with a hydroxyl group or a methoxy group. A fatty acid selected from the following is preferably used as the substituted fatty acid:

TABLE 3

Additional exemplary F groups which may provide Ra, Rb and/or Rc.

| Fatty acid | Ra, Rb and/or Rc = |
|---|---|
| F21 Ricinoleic acid [(12-hydroxy-(Z)-octadec-9-enoic acid | |
| F22 12-Hydroxy-octadecanoic acid | |

Fatty acid triglycerides of formula (II) in which at least one of the residues Ra, Rb and/or Rc denotes one of the residues F21 or F22 are particularly preferred.

A further particularly preferred example is therefore an agent for coloring and optionally simultaneously lightening keratinic fibers, which is characterized in that it includes as the fatty acid triglyceride (b) at least one compound of the general formula (II):

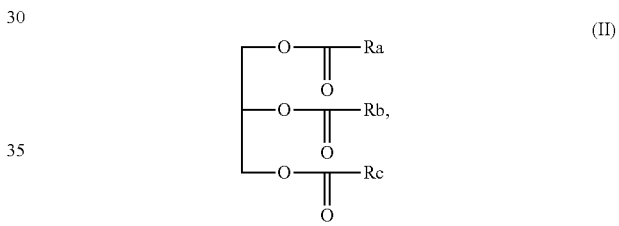

in which:

Ra, Rb, Rc independently of one another, denote a saturated or unsaturated, unbranched or branched, unsubstituted or substituted $C_7$-$C_{23}$ alkyl group, in which Ra, Rb and/or Rc are preferably selected from —$C_{13}H_{27}$ (F4), —$C_{15}H_{31}$ (F5), —$C_{17}H_{35}$ (F6), —$C_{19}H_{39}$ (F7) and the residues F12, F13, F16, F17, F21 and F22.

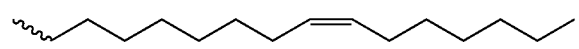

F12

-continued

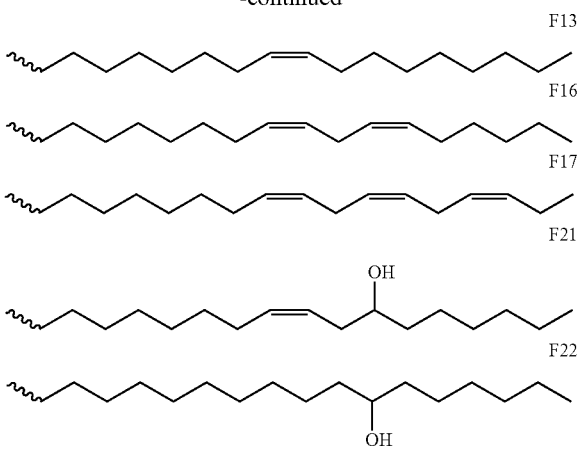

A further particularly preferred example is an agent for coloring, and optionally simultaneously lightening, keratinic fibers, which is characterized in that it includes as the fatty acid triglyceride (b) at least one compound of the general formula (II) in which at least one of the residues Ra, Rb and/or Rc denotes a mono- or polyunsaturated $C_{14}$-$C_{20}$ alkyl group, which may optionally be substituted with at least one functional group. Preferably, Ra, Rb and/or Rc denotes a hydroxyl group-substituted $C_{14}$-$C_{20}$ alkyl group.

In one example of the present specification, the agent includes as the fatty acid triglyceride (b) at least one triester of glycerol and three structurally identical fatty acids.

In a further example of the present specification the agent according to the present specification includes as the fatty acid triglyceride (b) at least one triester of glycerol with two different fatty acids. Agents according to the present specification including a fatty acid triglyceride (b) obtained by esterification of three different fatty acids with glycerol have likewise proved advantageous with respect to the application properties of the coloring agent.

The triesters are preferably selected from glycerol and the fatty acids disclosed with compound numbers 1 to 863 in the table on pages 13 to 38 of the priority document (DE 102011089220.6, incorporated herein by reference above).

For example, the structure of fatty acid triglyceride no. 863 in the table of the priority document is composed of glycerol and the fatty acid residues Ra=F22, Rb=F21 and Rc=F17, resulting in structure ($II_{863}$). The structures of all further derivatives may be derived in the same way.

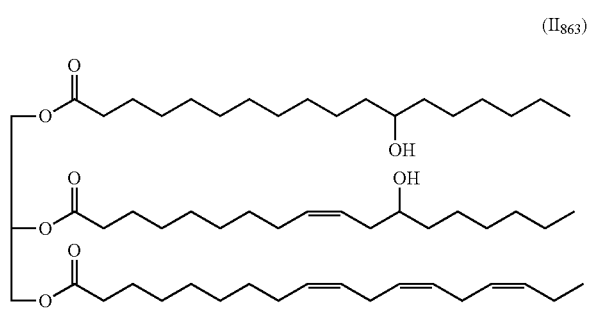

($II_{863}$)

In a further most particularly preferred example, mixtures of different fatty acid triglycerides (b) are used. It has been found that oils and/or fats whose triglyceride fraction has a special fatty acid distribution meet the requirements for these active ingredients to a special degree.

Particularly suitable mixtures of fatty acid triglycerides (b) in this context are above all the mixtures in which the compositions include glycerol and various fatty acids correspond to naturally occurring oils and fats.

The triglycerides or mixtures thereof derived from soybean oil, groundnut oil, olive oil, sunflower oil, macadamia nut oil, moringa oil, apricot kernel oil, marula oil and/or castor oil which may be optionally hydrogenated are particularly suitable for use in the agents according to the present specification.

Soybean oil includes a mixture of triglycerides bearing fatty acids selected from palmitic acid (F5), stearic acid (F6), oleic acid (F13), linoleic acid (F16) and linolenic acid (F17). As the use of soybean oil in the agents according to the present specification has proved to be particularly advantageous for producing intense and caring colors, mixtures of fatty acid glycerides of formula (II) in which the residues Ra, Rb and/or Rc denote F5, F6, F13 and/or F17 are particularly suitable.

Brilliant and intense colors having a particular care effect and particularly good wash fastness were also obtained using groundnut oil in the agents according to the present specification. Groundnut oil includes a mixture of triglycerides wherein the esterified fatty acids are principally composed of palmitic acid (F5), stearic acid (F6), behenic acid (F8), lignoceric acid (F9), oleic acid (F13) and linoleic acid (F16), which are esterified with glycerol. Thus agents including a mixture of fatty acid glycerides of formula (II) in which the residues Ra, Rb and/or Rc denote fatty acid residues selected from F5, F6, F8, F9, F13 and F16 are also extremely suitable.

Coloring results with outstanding wash fastness and care performance were likewise obtained using olive oil in the coloring agents according to the present specification. Olive oil includes fatty acid triglycerides wherein the esterified fatty acids are primarily myristic acid (F4), palmitic acid (F5), oleic acid (F13) and linoleic acid (F16). Coloring agents including a mixture of fatty acid triglycerides of formula (II) in which the residues Ra, Rb and/or Rc are selected from F4, F5, F13 and/or F16 have therefore likewise proved to be preferred in the context of the present specification.

Sunflower oil is likewise particularly suitable for use in the coloring agents according to the present specification. Sunflower oil mainly includes fatty acid triglycerides wherein the esterified fatty acids are primarily palmitic acid (F5), stearic acid (F6), oleic acid (F13) and linoleic acid (F16). Mixtures of fatty acid triglyceride esters (b) of formula (II) are thus particularly preferred in which the residues Ra, Rb and/or Rc are selected from F5, F6, F13 and F16.

The use of macadamia nut oil in the agents according to the present specification is moreover very suitable for producing stable, particularly wash-fast, caring and high-shine colors. In the fatty acid triglycerides of macadamia nut oil, the esterified fatty acids are primarily linoleic acid (F16), palmitic acid (F5), arachidic acid (F7), and stearic acid (F6). Thus mixtures of fatty acid triglyceride esters (b) of formula (II) in which Ra, Rb and/or Rc are selected from the fatty acid residues F16, F5, F7 and F6 are likewise particularly preferred.

Moringa oil includes a mixture of fatty acid triglycerides obtained by esterifying glycerol with the fatty acids selected from myristic acid (F4), palmitic acid (F5), stearic acid (F6), behenic acid (F8), oleic acid (F13) and linoleic acid (F16). Thus, mixtures of fatty acid triglyceride esters (b) of formula (II) are likewise most particularly preferred in which Ra, Rb and/or Rc are selected from the fatty acid residues F4, F5, F6, F8, F13 and F16. The colors obtained with the addition of moringa oil are likewise characterized by high-shine color results and exceptionally good wash fastness.

Apricot kernel oil includes as its main components triglycerides bearing the fatty acids oleic acid (F13) and linoleic acid (F16). Mixtures of fatty acid triglycerides (b) of formula (II) in which Ra, Rb and/or Rc are selected from the fatty acid residues F13 and F16 have likewise had an advantageous effect on the wash fastness, shine and feel of hair colored with the agents according to the present specification.

Marula oil substantially includes fatty acid triglycerides wherein the esterified fatty acids are primarily palmitic acid (F5), stearic acid (F6), oleic acid (F13) and linoleic acid (F16), and is likewise exceptionally suitable for producing intense, high-shine colors with excellent wash fastness. For that reason, mixtures of fatty acid triglyceride esters (b) of formula (II) are likewise preferred in which Ra, Rb and/or Rc are selected from the fatty acid residues F5, F6, F13 and F16.

Finally, colors obtained through the use of combinations of cationic anthraquinone dyes of formula (I) with hydrogenated and/or non-hydrogenated castor oil are also characterized by outstanding wash fastness, high shine and good care.

Castor oil consists predominantly of a triglyceride wherein the esterified fatty acids are primilary ricinoleic acid (F21), which is converted by hydrogenation to 12-hydroxy-octadecanoic acid (F22).

Thus, mixtures of fatty acid triglyceride esters (b) of formula (II) are moreover most particularly preferred in which Ra, Rb and/or Rc are selected from the fatty acid residues F21 and/or F22.

A further particularly preferred example is therefore an agent for coloring, and optionally simultaneously lightening hair, which is characterized in that it includes as the fatty acid triglyceride (b) a naturally occurring fatty acid triglyceride and/or mixtures of naturally occurring fatty acid triglycerides, which are included in soybean oil, groundnut oil, olive oil, sunflower oil, macadamia nut oil, moringa oil, apricot kernel oil, marula oil and/or optionally hydrogenated castor oil.

Within the above group, macadamia nut oil and (optionally hydrogenated) castor oil should be identified as being most particularly preferred.

The agents according to the present specification for coloring and/or lightening keratinic fibers include the fatty acid triglyceride(s) in an amount of from 0.001 to 15 wt. %, preferably from 0.05 to 12 wt. %, particularly preferably from 0.1 to 10.0 wt. %, in particular from 0.5 to 5.0 wt. %, and in particular preferably from 0.75 to 3.0 wt. %, relative in each case to the total weight of the agent. The specified proportions by weight relate here to the total amount of all fatty acid triglycerides included in the agent.

A further preferred example is therefore an agent for coloring and optionally simultaneously lightening keratinic fibers, which is characterized in that it includes the fatty acid triglyceride(s) in an amount of from 0.001 to 15 wt. %, preferably from 0.05 to 12 wt. %, particularly preferably from 0.1 to 10.0 wt. %, in particular from 0.5 to 5.0 wt. %, and in particular preferably from 0.75 to 3.0 wt. %, relative in each case to the total weight of the agent.

In a further preferred example the agents according to the present specification additionally include, in addition to the dye of formula (I), at least one further substantive dye. Substantive dyes may be divided into anionic, cationic and non-ionic substantive dyes. The substantive dyes are preferably selected from nitrophenylenediamines, nitroaminophenols, azo dyes, anthraquinones, triarylmethane dyes or indophenols and physiologically acceptable salts thereof. The additional substantive dyes are each preferably used in an amount of from 0.001 to 2 wt. %, relative to the total application preparation.

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, as well as substantive dyes including a heterocyclic compound having at least one quaternary nitrogen atom, in particular Basic Yellow 87, Basic Orange 31 and Basic Red 51. The cationic substantive dyes which are sold under the ARIANOR® trademark are likewise preferred cationic substantive dyes according to the present specification.

Non-ionic nitro and quinone dyes and neutral azo dyes in particular are suitable as non-ionic substantive dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Coloring results with outstanding color intensity, brilliance and good wash fastness are obtained in particular if the agents according to the present specification include as the further substantive dye at least one dye selected from D&C Red No. 33 (Acid Red 33), Acid Black No. 1, D&C Orange No. 4 (Acid Orange No. 4), Acid Red 18, Basic Red 76, Acid Violet 43, HC Blue No. 12, N-(2-hydroxethyl)-4-methyl-2-nitroaniline (Methyl Yellow), HC Yellow No. 2, Red B 54 and 2-amino-6-chloro-4-phenol.

The agents according to the present specification may moreover also be used as oxidation coloring agents. Such oxidation coloring agents additionally include at least one oxidation dye precursor, preferably at least one oxidation dye precursor of the developer type and at least one oxidation dye precursor of the coupler type. Particularly suitable oxidation dye precursors of the developer type are selected from at least one compound from the group formed from p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically acceptable salts thereof.

Particularly suitable oxidation dye precursors of the coupler type are selected from the group formed from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

The substantive dyes, developer components and coupler components are preferably each used in an amount of from 0.0001 to 5.0 wt. %, preferably from 0.001 to 2.5 wt. %, relative in each case to the ready-to-use agent. Developer components and coupler components may be used in approximately molar amounts to one another. Although the molar use has proved convenient, a certain excess of individual oxidation dye precursors is not disadvantageous, such that developer components and coupler components may be in a molar ratio of 1 to 0.5 to 1 to 3, in particular 1 to 1 to 1 to 2.

In the case of oxidation coloring agents, the agents preferably include an oxidizing agent, preferably hydrogen peroxide. The amounts of hydrogen peroxide correspond to the amounts in the lightening agents according to the present specification.

The coloring agents may moreover be used as lightening coloring agents. In order to achieve the lightening effect, the agents include hydrogen peroxide and/or one of the solid addition products thereof with organic or inorganic compounds.

A further example of the first subject matter of the present specification is therefore characterized in that the agent additionally includes hydrogen peroxide and/or one of the solid addition products thereof with organic or inorganic compounds.

In a preferred example, hydrogen peroxide itself is preferably used as an aqueous solution. 6 to 12 wt. % solutions in water are preferably used. Ready-to-use agents of the first subject matter of the present specification that are preferred according to the present specification are characterized in that they include an amount of from 0.5 to 20 wt. %, preferably from 1 to 12.5 wt. %, particularly preferably from 2.5 to 10 wt. % and in particular from 3 to 6 wt. % of hydrogen peroxide, relative in each case to the total weight of the ready-to-use agent.

In order to achieve a stronger lightening and bleaching effect, the agent may also include at least one peroxo salt. Suitable peroxo salts are inorganic peroxo compounds, preferably selected from the group formed from ammonium peroxodisulfate, alkali metal peroxodisulfates, ammonium peroxomonosulfate, alkali metal peroxomonosulfates, alkali metal peroxodiphosphates and alkaline-earth metal peroxides. Peroxodisulfates are particularly preferred, in particular ammonium peroxodisulfate, potassium peroxodisulfate and sodium peroxodisulfate.

The persulfates are each included in the agent according to the present specification in an amount of from 0.5 to 20 wt. %, preferably from 1 to 12.5 wt. %, particularly preferably from 2.5 to 10 wt. % and in particular from 3 to 6 wt. %, relative in each case to the total weight of the ready-to-use agent.

A further preferred example is an agent for coloring and simultaneously lightening keratinic fibers, which additionally includes hydrogen peroxide, one of the solid addition products thereof with organic or inorganic compounds, ammonium peroxodisulfate, potassium peroxodisulfate and/or sodium peroxodisulfate, each in an amount from 0.5 to 20 wt. %, preferably 1 to 12.5 wt. %, particularly preferably 2.5 to 10 wt. % and in particular 3 to 6 wt. %, relative to the total weight of the ready-to-use agent.

The ready-to-use coloring agents may also include additional active ingredients, auxiliary substances and additives to improve the coloring capacity and to establish further desired properties of the agents.

The ready-to-use coloring agents are preferably provided as a liquid preparation and therefore a surface-active substance is additionally added to the agents, such surface-active substances being referred to as surfactants or emulsifiers, depending on the field of application. They are preferably selected from anionic, cationic, zwitterionic, amphoteric and non-ionic surfactants and emulsifiers.

Agents that are preferred according to the present specification are characterized in that the agent additionally includes at least one anionic surfactant. Preferred anionic surfactants are fatty acids, alkyl sulfates, alkyl ether sulfates and ether carboxylic acids with 10 to 20 carbon atoms in the alkyl group and up to 16 glycol ether groups in the molecule. The anionic surfactants are used in an amount of from 0.1 to 45 wt. %, preferably from 1 to 30 wt. % and most particularly preferably from 1 to 15 wt. %, relative to the total amount of the ready-to-use agent.

Agents that are preferred according to the present specification are characterized in that the agent additionally includes at least one zwitterionic surfactant. Preferred zwitterionic surfactants are betaines, N-alkyl-N,N-dimethylammonium glycinates, N-acyl aminopropyl-N,N-dimethylammonium glycinates, and 2-alkyl-3-carboxymethyl-3-hydroxyethyl imidazolines. A preferred zwitterionic surfactant is known under the INCI name Cocamidopropyl Betaine.

Agents that are preferred according to the present specification are characterized in that the agent additionally includes at least one amphoteric surfactant. Preferred amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids. Particularly preferred amphoteric surfactants are N-cocoalkyl aminopropionate, cocoacylaminoethyl aminopropionate and $C_{12}$-$C_{18}$ acyl sarcosine.

It has moreover proved advantageous for the agents to include further, non-ionogenic interfacially-active substances. Preferred non-ionic surfactants are alkyl polyglycosides as well as alkylene oxide addition products with fatty alcohols and fatty acids, each including 2 to 30 mol of ethylene oxide per mol of fatty alcohol or fatty acid. Preparations having outstanding properties are likewise obtained if they include fatty acid esters of ethoxylated glycerol as non-ionic surfactants.

The non-ionic, zwitterionic or amphoteric surfactants are used in an amount of from 0.1 to 45 wt. %, preferably from 1 to 30 wt. % and most particularly preferably from 1 to 15 wt. %, relative to the total amount of the ready-to-use agent.

Agents that are suitable according to the present specification may also include cationic surfactants of the quaternary ammonium, esterquat and amidoamine types. Preferred quaternary ammonium compounds are ammonium halides and the imidazolium compounds known under the INCI names Quaternium-27 and Quaternium-83. Further cationic surfactants which may be used according to the present specification are the quaternized protein hydrolysates. A compound from the amidoamines that is particularly suitable according to the present specification is stearamidopropyl dimethylamine, which is commercially available under the name Tegoamid® S 18. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. The cationic surfactants are preferably included in the agents used according to the present specification in an amount of from 0.05 to 10 wt. %, relative to the total agent.

The ready-to-use coloring agents may include further auxiliary substances and additives. Thus it has proved advantageous if the agents include at least one thickening agent. There are no restrictions in principle regarding these thickening agents. Both organic and also purely inorganic thickening agents may be used.

Suitable thickening agents are
anionic polymers,
cationic, synthetic polymers;
naturally occurring thickening agents, such as non-ionic guar gums, scleroglucan gums or gum arabic, ghatti gum, karaya gum, tragacanth gum, carrageen gum, carob seed meal, pectins, starch fractions and derivatives such as amylose, amylopectin and dextrins, as well as non-ionic cellulose derivatives, such as for example methyl cellulose and hydroxyalkyl celluloses;
non-ionic, fully synthetic polymers, such as polyvinyl alcohol or polyvinylpyrrolidone; as well as
inorganic thickening agents, in particular phyllosilicates such as for example bentonite, particularly smectites, such as montmorillonite or hectorite.

Coloring processes on keratin fibers conventionally take place in an alkaline environment. In order to protect the keratin fibers and also the skin as far as possible, it is not desirable to establish too high a pH, however. The pH of the agents according to the present specification may therefore be between 3 and 11. It is preferable for the pH of the ready-to-use agent to be between 5 and 11, in particular between 5 and 7. The pH values in the context of the present specification are pH values measured at a temperature of 22 degrees Celsius (° C.).

The alkalizing agents which may be used according to the present specification to establish the preferred pH may be selected from the group formed from ammonia, alkanolamines, basic amino acids, as well as inorganic alkalizing agents such as alkaline-earth/alkali metal hydroxides, alkaline-earth/alkali metal metasilicates, alkaline-earth/alkali metal phosphates and alkaline-earth/alkali metal hydrogen phosphates. Preferred inorganic alkalizing agents are magnesium carbonate, sodium hydroxide, potassium hydroxide, sodium silicate and sodium metasilicate. Organic alkalizing agents that may be used according to the present specification are preferably selected from monoethanolamine, 2-amino-2-methylpropanol and triethanolamine. The basic amino acids that may be used as the alkalizing agent according to the present specification are preferably selected from the group formed from arginine, lysine, ornithine and histidine, particularly preferably arginine. In the context of the investigations leading to the agents of the present disclosure it has however been found that preferred agents according to the present specification are furthermore characterized in that they additionally include an organic alkalizing agent. One example of the first subject matter of the present specification is characterized in that the agent additionally includes at least one alkalizing agent which is selected from the group formed from ammonia, alkanolamines and basic amino acids, in particular from ammonia, monoethanolamine and arginine or the acceptable salts thereof.

It has furthermore proved advantageous for the coloring agents, in particular if they additionally include hydrogen peroxide, to include at least one stabilizer or complexing agent. Particularly preferred stabilizers are phenacetin, alkali benzoates (sodium benzoate) and salicylic acid. All prior art complexing agents may also be used. Preferred complexing agents according to the present specification are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

The agents according to the present specification may moreover include further active ingredients, auxiliary agents and additives, such as for example non-ionic polymers, such as for example vinylpyrrolidone/vinyl acrylate copolymers, polyvinylpyrrolidone, vinylpyrrolidone/vinyl acetate copolymers, polyethylene glycols and polysiloxanes; additional silicones, such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidone copolymers quaternized with diethyl sulfate, vinylpyrrolidone-imidazolinium-methochloride copolymers and quaternized polyvinyl alcohol; zwitterionic and amphoteric polymers; structuring agents such as glucose, maleic acid and lactic acid, hair-conditioning compounds such as phospholipids, for example lecithin and cephalins; perfume oils, dimethyl isosorbide and cyclodextrins; active ingredients to improve the fiber structure, in particular mono-, di- and oligosaccharides; dyes for coloring the agent; anti-dandruff active ingredients such as piroctone olamine, zinc omadine and climbazole; amino acids and oligopeptides; protein hydrolysates of animal and/or plant origin, light stabilizers and UV blockers; active ingredients such as panthenol, pantothenic acid, pantolactone, allantoin, pyrrolidone carboxylic acids and salts thereof as well as bisabolol; polyphenols, in particular hydroxycinnamic acids, vitamins, pro-vitamins and vitamin precursors; plant extracts; beeswax, montan wax and paraffins; swelling and penetrating substances such as glycerol, propylene glycol monoethyl ether, carbonates, hydrogen carbonates, guanidines, pearlescent agents such as ethylene glycol mono- and distearate and PEG-3 distearate; pigments as well as propellants such as propane-butane mixtures, $N_2O$, dimethyl ether, $CO_2$ and air.

Further substances may be selected in accordance with the desired properties of the agents. With regard to further optional components and to the amounts of these components used, reference is expressly made to the relevant manuals, for example Kh. Schrader, Grundlagen and Rezepturen der Kosmetika [Fundamentals and formulations of cosmetics], $2^{nd}$ Edition, Hüthig Buch Verlag, Heidelberg, 1989.

The additional active ingredients and auxiliary substances are used in the agents according to the present specification preferably in amounts of from 0.0001 to 25 wt. % in each case, in particular from 0.0005 to 15 wt. %, relative to the total weight of the application mixture.

A method for coloring keratinic fibers, in particular human hair, which is characterized in that an agent of the first subject matter of the present specification is applied to the keratin-containing fibers, left on the fibers for from 5 to 60 minutes and then rinsed out again with water or washed out with a shampoo, is suitable in particular for the application of the agents according to the present specification. The contact time of the ready-to-use coloring agents is preferably from 5 to 45 minutes, in particular from 10 to 40 minutes, particularly preferably from 15 to 35 minutes. At the end of the contact time the remaining coloring preparation is rinsed out of the hair with water or a cleaning agent.

The agents according to the present specification may be formulated as one-component agents (coloring and lightening agent) or as multi-component agents such as two-component agents or three-component agents, and used accordingly. A separation into multi-component systems is useful in particular where incompatibilities between the ingredients are to be expected or of concern; in such systems, the agent to be used is prepared by the consumer immediately before use by mixing the components together.

If the agent according to the present specification includes both substantive dyes—as well as optionally additionally oxidation dye precursors—and oxidizing agents, they are conveniently packaged separately from one another in order to avoid a premature, undesired reaction and brought into contact only immediately before application.

A coloring and lightening method in which the coloring cream and the oxidizing agent are initially separate is therefore preferred. The present specification therefore also provides a method for coloring and lightening human hair, wherein a composition on an aqueous basis including hydrogen peroxide is mixed with an agent according to the present specification including at least one compound of formula (I) to form a homogeneous composition, and this is applied to the hair. The fatty acid triglyceride (b) may in this case be packaged with the hydrogen peroxide solution, with the compound of formula (I), or with both.

In a further example of the present specification, agents are therefore preferred which are characterized in that they are produced immediately before application by mixing at least two preparations, wherein the at least two preparations are provided in at least two separately packaged containers, and wherein one container contains an agent (A), which includes in a cosmetic carrier at least one cationic anthraquinone dye of formula (I), optionally including oxidation dye precursors as well, and a further container contains an oxidizing agent preparation (B) including at least one oxidizing agent. The fatty acid triglycerides (b) may in this case be packaged together with the cationic anthraquinone dye of formula (I) in container (A), together with the oxidizing agent preparation in container (B), or both.

The formulation of a combination of (a) compounds of the general formula (I) with (b) fatty acid triglycerides is outstandingly suitable for producing intense colors with high brilliance, high shine and a low selectivity in conjunction with an outstanding wash fastness. The agents are likewise outstandingly suitable for minimizing or preventing the drying out of the scalp.

The present specification also provides the use of an agent of the first subject matter of the present specification to produce hair dyes having increased shine, an intense color result with improved fastness properties and/or reduced selectivity.

All that has been stated in respect of the agents according to the present specification applies with necessary alterations to further preferred examples of the methods and use according to the present specification.

EXAMPLES

The examples that follow indicate agents that were produced according to the present specification for the treatment of keratinous fibers. Unless otherwise indicated, the stated quantities are percentages by weight.

Formulation Example 1

| Description | wt. % |
| --- | --- |
| Polyquaternium-10 | 0.45 |
| Citric acid monohydrate | 0.70 |
| Timiron Super Silver | 0.20 |
| Cationic Blue 347 | 0.20 |
| Salicylic acid | 0.20 |
| Disodium cocoamphodiacetate | 7.00 |
| Sodium benzoate | 0.50 |
| Nicotinamide | 0.50 |
| Sodium pyrrolidone-2-carboxylate | 2.00 |
| Cutina HR | 1.00 |
| PEG-7 glyceryl cocoate | 0.50 |
| Sodium myreth sulfate (2 EO), 70% | 24.00 |
| NaOH, 50% | 0.15 |
| D-Panthenol, 75% | 0.50 |
| Euperlan PK 3000 AM | 2.60 |
| ProSina | 2.00 |
| Sericin H | 0.20 |
| Caramel syrup, 75% | 0.60 |
| Apricot kernel oil | 0.10 |
| PEG-40 hydrogenated castor oil | 0.60 |
| Sodium chloride | 0.20 |
| Antil 141 L | 1.00 |
| Hydrolyzed silk protein | 1.50 |
| Benzophenone-4 | 0.50 |
| Perfume | qs |
| Water | to 100 |

Formulation Example 2

| Description | wt. % |
|---|---|
| Cetearyl alcohol | 6.00 |
| Coconut alcohol | 6.00 |
| Ceteareth-12 | 2.00 |
| Ceteareth-20 | 3.00 |
| PEG-40 hydrogenated castor oil | 2.00 |
| Macadamia nut oil | 1.00 |
| Methylparaben | 0.15 |
| Propylparaben | 0.15 |
| Tocopherol | 0.20 |
| Phenoxyethanol | 1.00 |
| HC Yellow No. 2 | 0.20 |
| N,N-Bis(2-hydroxyethyl)-2-nitro-p-phenylenediamine | 0.10 |
| Hydroxyethylcellulose | 1.00 |
| NaOH, 50% | 0.10 |
| Polyethylene glycol MG 400 | 5.00 |
| HC Blue No. 2 | 1.50 |
| Basic Blue 99 | 0.42 |
| Basic Brown 16 | 0.08 |
| D&C Violet No. 2 | 0.08 |
| Basic Red 76 | 0.08 |
| Basic Yellow 57 | 0.08 |
| D-Panthenol, 75% | 0.30 |
| Citric acid monohydrate | 0.10 |
| Cationic Blue 347 | 0.50 |
| Perfume | qs |
| Water | to 100 |

Formulation Example 3

| Description | wt. % |
|---|---|
| Cetearyl alcohol | 6.00 |
| Coconut alcohol | 6.00 |
| Ceteareth-12 | 2.00 |
| Ceteareth-20 | 3.00 |
| PEG-40 hydrogenated castor oil | 2.00 |
| Macadamia nut oil | 1.00 |
| Methylparaben | 0.15 |
| Propylparaben | 0.15 |
| Tocopherol | 0.20 |
| Phenoxyethanol | 1.00 |
| Hydroxyethylcellulose | 1.00 |
| NaOH, 50% | 0.10 |
| Polyethylene glycol MG 400 | 5.00 |
| HC Blue No. 12 | 1.20 |
| Bluequat Bromide | 0.21 |
| Basic Brown 17 | 0.08 |
| D&C Violet 2 | 0.08 |
| Basic Red 76 | 0.08 |
| Basic Yellow 57 | 0.08 |
| HC Yellow No. 2 | 0.20 |
| N,N-Bis(2-hydroxyethyl)-2-nitro-p-phenylenediamine | 0.20 |
| D-Panthenol, 75% | 0.30 |
| Citric acid monohydrate | 0.10 |
| Cationic Blue 347 | 0.50 |
| Perfume | qs |
| Water | to 100 |

Recipe Constituents

| | |
|---|---|
| Cationic Blue 347 | 3-[(4-amino-9,10-dihydro-3-methyl-9,10-dioxo-1-anthracenyl)amino]-N,N,N-trimethyl-1-propanaminium methosulfate |
| Bluequat Bromide | 3-{[9,10-dihydro-4-(methylamino)-9,10-dioxo-1-anthracenyl]amino}-N,N-dimethyl-N-propyl-1-propanaminium bromide |
| Timiron Super Silver | INCI name: Mica, Titanium Dioxide (Merck KGaA) |
| Cutina HR | INCI name: Hydrogenated castor oil (BASF) |
| Euperlan PK 3000 AM | approx. 43% solid substance; INCI name: Aqua, Glycol Distearate, Glycerin, Laureth-4, Cocamidopropyl Betaine, Formic Acid (BASF) |
| ProSina | INCI name: Aqua, hydrolyzed Keratin (Keratec/Croda) |
| Sericin H | INCI name: Sericin (Pentapharm) |
| Antil141 L | approx. 40% active substance; INCI name: Propylene Glycol, PEG-55 Propylene Glycol Oleate (Goldschmidt/Evonik) |

The coloring formulations were applied to hair strands and left there for 30 minutes at room temperature. Then the fibers were rinsed thoroughly with water and dried.

The treated fibers were characterized by intense colors with high shine, an outstanding wash fastness and a soft feel.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability or configuration of the invention in any way. Rather, the foregoing detailed description will provide those skilled in the art with a convenient road map for implementing an exemplary embodiment of the invention, it being understood that various changes may be made in the function and arrangement of the elements described in an exemplary embodiment without departing from the scope of the invention as set forth in the appended claims and their legal equivalents.

The invention claimed is:

1. An agent for coloring keratinic fibers comprising, in a cosmetic carrier,
   (a) at least one compound of formula (I):

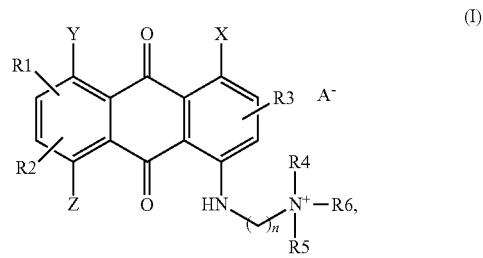

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group,
in which:
R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
wherein at least one of the residues X, Y and Z denotes an N(R7)(R8) group;
n denotes an integer between 2 and 6 inclusive; and
$A^-$ denotes a physiologically acceptable anion;
and
(b) from 0.01 to 15 wt. %, relative to the total weight of the agent, of at least one fatty acid triglyceride.

2. The agent of claim 1, wherein the agent simultaneously lightens the keratinic fibers.

3. The agent of claim 1, wherein at least one of the residues R1, R2 and R3 of formula (I) denotes a $C_1$-$C_6$ alkyl group.

4. The agent of claim 1, wherein X of formula (I) denotes an $NH_2$ group.

5. The agent of claim 1, wherein the compound of formula (I) is provided by a compound according to formula (Ia),

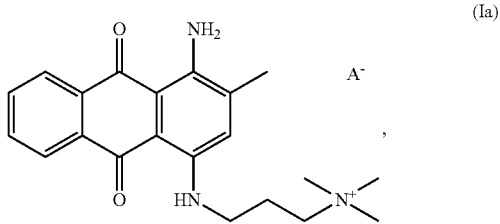

in which $A^-$ denotes a physiologically acceptable anion.

6. The agent of claim 1, wherein the compound(s) according to formula (I) comprise an amount of from 0.0001 to 5 weight percent (wt. %), relative to the total weight of the agent.

7. The agent of claim 1, wherein the compound(s) according to formula (I) comprise an amount of from 0.005 to 3.5 wt. %, relative to the total weight of the agent.

8. The agent of claim 1, wherein the compound(s) according to formula (I) comprise an amount of from 0.01 to 2.5 wt. %, relative to the total weight of the agent.

9. The agent of claim 1, wherein the fatty acid triglyceride (b) is provided by at least one compound of formula (II):

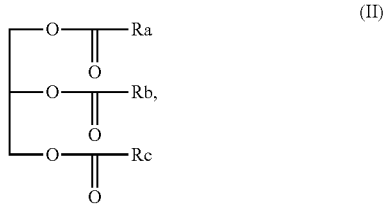

in which:
Ra, Rb, Rc independently of one another, denote a saturated or unsaturated, unbranched or branched, unsubstituted or substituted $C_7$-$C_{23}$ alkyl group.

10. The agent of claim 9, wherein Ra, Rb and Rc are selected from the group consisting of $-C_{13}H_{27}$, $-C_{15}H_{31}$, $-C_{17}H_{35}$, $-C_{19}H_{39}$ and the residues F12, F13, F16, F17, F21 and F22

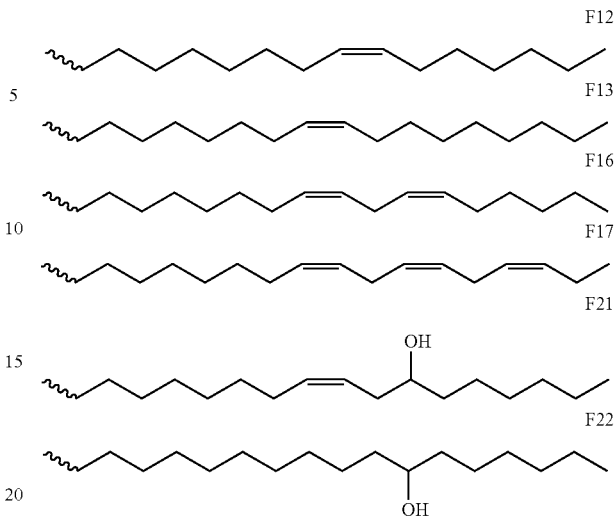

11. The agent of claim 9, wherein at least one of the residues Ra, Rb and Rc denotes a mono- or polyunsaturated $C_{14}$-$C_{20}$ alkyl group, which may optionally be substituted with at least one functional group.

12. The agent of claim 9, wherein at least one of the residues Ra, Rb and Rc is substituted with a hydroxyl group.

13. The agent of claim 1, wherein the fatty acid triglyceride(s) (b) comprises a naturally occurring fatty acid triglyceride or a mixture of naturally occurring fatty acid triglycerides, wherein at least one of the naturally occurring fatty acid triglycerides is derived from soybean oil, groundnut oil, olive oil, sunflower oil, macadamia nut oil, moringa oil, apricot kernel oil, marula oil, castor oil, or hydrogenated castor oil.

14. The agent of claim 1, wherein the fatty acid triglyceride(s) (b) comprise an amount of from 0.5 to 0.5 wt. %, relative to the total weight of the agent.

15. The agent of claim 1, wherein the fatty acid triglyceride(s) (b) comprise an amount of from 0.05 to 12 wt. %, relative to the total weight of the agent.

16. The agent of claim 1, wherein the fatty acid triglyceride(s) (b) comprise an amount of from 0.1 to 10.0 wt. %, relative to the total weight of the agent.

17. The agent of claim 1, further comprising at least one additional substantive dye, in addition to the dye of formula (I).

18. The agent of claim 17, wherein the at least one additional substantive dye is selected from the group consisting of Basic Blue 7, Basic Blue 26, Basic Violet 2, Basic Violet 14, Basic Yellow 57, Basic Red 76, Basic Blue 99, Basic Brown 16, Basic Brown 17, Basic Yellow 87, Basic Orange 31 and Basic Red 51, HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9,1,4-diamino-2-nitrobenzene, 2-amino-4-nitrophenol, 1,4-bis-(2-hydroxyethyl)amino-2-nitrobenzene, 3-nitro-4-(2-hydroxy-ethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3- nitrophenol, 4-nitro-o-phenylene diamine, 6-nitro-1,2,3,4-tetrahydroquinoxaline, 2-hydroxy-1,4-naphthoquinone, picramic acid and salts thereof, 2-amino-6-chloro-4- nitrophenol, 4-ethylamino-3-nitrobenzoic acid and 2-chloro-6-ethylamino-4-nitrophenol, D&C Red No. 33 (Acid Red 33), Acid Black No. 1, D&C Orange No. 4 (Acid Orange No. 4), Acid Red 18, Acid Violet 43, N-(2-hydroxyethyl)-4-methyl-2-nitroaniline (Methyl Yellow), Red B 54, and combinations thereof.

19. The agent of claim 1, wherein the pH of the agent is between 5 and 7.

20. A method of dyeing keratinic fibers to produce increased shine, an intense color result with improved fastness properties, or reduced selectivity, comprising:
(A) applying an agent for coloring, and optionally simultaneously lightening, keratinic fibers comprising, in a cosmetic carrier,
(i) at least one compound of formula (I):

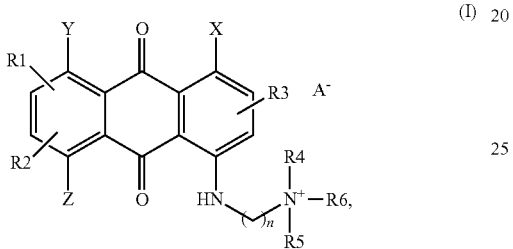

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:
R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
wherein at least one of the residues X, Y and Z denotes an N(R7)(R8) group;

n denotes an integer between 2 and 6 inclusive; and
$A^-$ denotes a physiologically acceptable anion;
and
(ii) from 0.001 to 15 wt. %, relative to the total weight of the agent, of at least one fatty acid triglyceride; and
(B) after a contact time, rinsing the agent from the keratinic fibers.

* * * * *